United States Patent [19]

Edmunds et al.

[11] Patent Number: 4,920,051
[45] Date of Patent: Apr. 24, 1990

[54] RECOVERY OF UROKINASE COMPOUNDS

[75] Inventors: Timothy Edmunds, Weymouth; Susan F. Foley, Brighton, both of Mass.

[73] Assignee: Damon Biotech, Inc., Needham Heights, Mass.

[21] Appl. No.: 205,437

[22] Filed: Jun. 10, 1988

Related U.S. Application Data

[63] Continuation-in-part of Ser. No. 151,707, Feb. 3, 1988.

[51] Int. Cl.⁵ .............................................. C12N 9/72
[52] U.S. Cl. ................................... 435/215; 435/212; 435/815; 424/94.63
[58] Field of Search ............... 435/215, 212, 226, 815; 424/94.63

[56] References Cited

U.S. PATENT DOCUMENTS

| | | | |
|---|---|---|---|
| 2,961,382 | 11/1960 | Singher et al. | 195/68 |
| 2,983,647 | 5/1961 | Kjeldgaard et al. | 167/73 |
| 2,989,440 | 6/1961 | Singher et al. | 195/66 |
| 3,081,236 | 3/1963 | Doczi | 195/66 |
| 3,256,158 | 6/1966 | White | 195/66 |
| 3,355,361 | 11/1967 | Lesuk | 195/62 |
| 3,930,944 | 1/1976 | Nicol | 195/1.7 |
| 3,930,945 | 1/1976 | Lewis | 195/1.7 |
| 4,066,506 | 1/1978 | Johnson et al. | 195/66 |
| 4,106,992 | 8/1978 | Vairel et al. | 195/66 |
| 4,169,764 | 10/1979 | Takezawa et al. | 435/215 |
| 4,190,708 | 2/1980 | Kuo et al. | 435/215 |
| 4,225,675 | 9/1980 | Nakamura et al. | 435/215 |
| 4,259,447 | 3/1981 | Häfeli | 435/215 |
| 4,259,448 | 3/1981 | Nakamura et al. | 435/215 |
| 4,317,882 | 3/1982 | Horiguchi et al. | 435/212 |
| 4,326,033 | 4/1982 | Holleman et al. | 435/212 |
| 4,328,314 | 5/1982 | Horiguchi et al. | 435/212 |
| 4,370,417 | 1/1983 | Hung et al. | |
| 4,381,346 | 4/1983 | Huasin et al. | 435/215 |
| 4,537,852 | 8/1985 | Sugimoto | 435/215 |
| 4,540,486 | 9/1985 | Ramsden | 210/198.2 |
| 4,606,825 | 8/1986 | Crane et al. | 210/635 |

FOREIGN PATENT DOCUMENTS

| | | |
|---|---|---|
| 92182 | 4/1983 | European Pat. Off. . |
| 0154272 | 9/1985 | European Pat. Off. . |
| 2121050A | of 1913 | United Kingdom . |

OTHER PUBLICATIONS

Nan, D. R. (1986), Biochromatography 1(2), 82–94.

Primary Examiner—Elizabeth C. Weimar
Assistant Examiner—Charles L. Patterson, Jr.
Attorney, Agent, or Firm—Lahive & Cockfield

[57] ABSTRACT

Disclosed is a method of recovering urokinase compounds from media and cell extracts. The method comprises contacting the urokinase compound-containing solution with a silicaceous matrix material comprising covalently bound polymer having plural anionic groups. Selective elution of the urokinase compound can produce elutants of high specific activity. The method can succeed in recovering greater than 90% of the urokinase activity from the crude solution.

14 Claims, 2 Drawing Sheets 1 2 3 4 5 6 7 8 9 10

1 2 3 4 5 6 7 8 9

RECOVERY OF UROKINASE COMPOUNDS

CROSS REFERENCE TO RELATED APPLICATION

This application is a continuation in part of application Ser. No. 151,707, filed Feb. 3, 1988, entitled "Recovery of Tissue Plasminogen Activator".

BACKGROUND OF THE INVENTION

The present invention relates to a method of recovering enzymatically active urokinase and prourokinase from a solution, such as a culture medium or cell extract, using a chromatography resin. The invention is based on the discovery that a type of resin developed originally to selectively bind immunoglobulins binds prourokinase and urokinase and can be selectively eluted, and therefore is useful for the commercial, large scale purification of prourokinase and urokinase from solutions containing these proteins.

Urokinase is a useful fibrinolytic agent for initiating the cascade mechanism which disrupts potentially fatal thrombosis. Urokinase is a two-chain glycoprotein having a molecular weight of approximately 32,000–34,000 daltons and a specific activity of about 250,000 CTA units per mg protein. It is an enzymatically active cleavage product of enzymatically inactive prourokinase. Prourokinase is a single chain glycoprotein having a molecular weight of approximately 45,000–55,000 daltons. Unlike urokinase, prourokinase is not active, but is specific for the site of the thrombus. Plasmin cleaves prourokinase to enzymatically active urokinase at that site.

Both forms have been isolated from the urine in a number of ways. One method includes treating the urine with a reagent (e.g., bentonite or other aluminum silicates) which cause the formation of urokinase-containing precipitates, and then eluting the urokinase from the precipitates. Other procedures include bringing the urine in contact with an absorbent reagent and subsequently eluting the absorbent. Known absorbent materials used for this purpose have included, for example, calcium carbonate, barium sulfate, aluminum oxide, calcium phosphate, zinc hydroxide, activated carbon, and hydrated aluminum silicates. Various cation exchange resins have also been useful for this purpose (e.g., U.S. Pat. Nos. 2,983,647; 2,989,440).

Exclusion chromatographic procedures have been practiced which have included the use of, for example, a DEAE cellulose resin or cross-linked dextran gels of the methacrylic-carboxylic acid type (e.g., U.S. Pat. No. 3,256,158). In such a procedure, the resin binds impure proteins and pyrogens, leaving the urokinase in solution.

More recently, affinity chromatographic methods have been practiced using various reagents having an affinity for urokinase bound or adhered to a water-insoluble solid support such as diatomaceous earth, agarose, cellulose, collagen, and other adsorbents. The affinity reagents include basic amino acids, agmatine, aprotinin, derivatives of guanidine and adenine, fibrin, and antibodies which recognize urokinase among many others.

Purification has also been attempted by various electrophoretic and HPLC means.

In an attempt to obtain clinically valuable amounts of urokinase compounds, cells which are known to produce these proteins (e.g., kidney and lung) have been cultured in vitro. Such cells include human and green or Rhesus monkey embryonic and adult kidney, adult and embryonic lung, adult and embryonic heart, placenta, adult thyroid, spleen, and ureter. However, the yield obtained from the culture media of these cells has still not been great, despite attempts to increase output by enriching the culture media with inducers (e.g., various amino acids, saccharides, hormones, fumaric acid, malic acid succinic acid, and/or glycolic acid), or to decrease proteolysis and denaturation (with, e.g., metal chelators, pronase, and trypsin inhibitors). Further attempts to increase the urokinase production of cultured cells were made by culturing urokinase-producing lymphoid hybridoma cells previously transplanted to and propagated in a non-human, warm-blooded animal in the presence of a urokinase inducer (U.S. Pat. No. 4,537,852). However, this process is expensive and time-consuming to practice.

With the advent of recombinant DNA technology, cell lines which have been genetically engineered to produce large amounts of prourokinase have been developed and cultured. These cell lines include microorganisms such as $E.\ coli$, yeast, Bacillus, and Neurospora, and mammalian cell lines including monkey and human kidney cells and fibroblasts. The expressed prourokinase must then be recovered in active form from the cell extract or liquid growth media into which it has been secreted. Recovery has been accomplished using essentially the same methodologies as described above for purification from urine.

Recovery from culture media is a significant undertaking in that such media typically contain many other unrelated proteins, some of which have proteolytic activity. For example, serum-supplemented media are known to contain plasmin and other serum proteases which readily degrade prourokinase. Most known purification procedures do not adequately protect urokinase compounds from proteolytic degradation, despite attempts to do so by the addition of metal chelators and various protease inhibitors. As described above, these precautions offer at best only partial protection. Accordingly, known recovery methods are most effective when used to isolate urokinase compounds from serum-free solutions, despite the fact that they are inefficient, and may introduce potentially toxic elements. In addition, purification procedures employing immunoaffinity chromatography may be quite costly when scaled up to meet commercial needs.

Therefore, for commercial quantities of urokinase compounds to be produced in an enzymatically active form, large scale purification procedures are required which effectively, efficiently, and rapidly recover it from the media before much of it is degraded.

Accordingly, it is an object of the invention to provide a rapid, simple, and commercially viable method of isolating a urokinase compound from a urokinase compound-containing solution. Another object is to provide a method of purifying urokinase compounds from culture media. Yet another object is to provide a method of recovering undegraded urokinase compounds substantially free of other non-related proteins from a urokinase compound-containing solution. It is also an object of the invention to provide a method of separating urokinase compounds from other proteins present in serum-supplemented media. It is a further object to provide a method of recovering undegraded urokinase compounds in amounts useful for the large scale commercial production of pharmaceutical formulations containing the same.

SUMMARY OF THE INVENTION

It has now been discovered that a chromatography resin of the type used to purify immunoglobulins is useful in recovering prourokinase and urokinase from prourokinase- and urokinase-containing solutions. ("Prourokinase", "urokinase", and mixtures thereof are hereinafter referred to as "urokinase compounds".) More specifically, it has been discovered that silicaceous matricies containing covalently bound polymers with multiple anionic groups surprisingly bind urokinase preferentially to many other proteinaceous components in a solution, and permit selective elution of fractions rich in urokinase compounds. The use of such matricies in simple batch or chromatographic procedures can expedite the recovery of urokinase compounds from urokinase compound-containing solutions by minimizing the time during which a urokinase compound may be in contact with degradative conditions in such urokinase including serum-free and serum-supplemented liquid culture media, extracts of cells which synthesize and intracellularly deposit urokinase, and other solutions containing albumin, proteases, immunoglobulins, and diverse other proteins. Quick separation of urokinase compounds from these other proteins minimize the time during which the urokinase compounds are in contact with degradative elements therein.

In its broadest aspects, this invention provides a method of recovering urokinase compounds from a urokinase compound-containing protein solution. This method includes contacting the urokinase compound-containing solution with a particulate, silicaceous matrix under conditions conducive for the binding of urokinase compounds to the matrix, separating unbound protein from the matrix, and releasing the bound urokinase compounds therefrom. The matrix comprises a covalently bound polymer having multiple anionic groups.

In one aspect, the present invention provides a method of recovering urokinase compounds from culture media, including those media which are supplemented with serum. Serum contains immunoglobulins which are known to bind to matrices of the type used in this invention, and serum proteases, which have the ability to degrade urokinase compounds. However, the matrix material used in this invention enables facile separation of urokinase compounds from harmful proteases, albumin, and other proteins by selective binding and elution as disclosed below.

The method of the present invention may be practiced by passing a urokinase compound-containing solution over the matrix using a chromatographic technique, i.e., disposing the matrix in a column which is loaded, washed, and subsequently harvested. Alternatively, the method can be conducted using a solid phase batch extraction technique wherein the matrix material and the urokinase compound-containing solution are mixed together.

The polymer which is covalently bound to the solid phase of the matrix of the present invention comprises, e.g., a polyethylene backbone, containing pendant anionic groups such as carboxylate groups. In a preferred embodiment, the polymer comprises a carboxylated polyethyleniminoalkyl trialkoxy silane, most preferably carboxylated polyethyleniminopropyl trimethoxysilane. The silane group is reactive and bonds covalently with free hydroxyl groups on the silica matrix. In this embodiment, the matrix is the reaction product of particulate pore glass or carboxylated silica and the polyethyleniminopropyl trimethoxy silane polymer having a molecular weight ranging from about 400 to about 1800 daltons. The glass may have an average particle diameter ranging from about 35 to 180 microns and an average pore size ranging from about 40 to 1000 Angstroms. Alternatively, the silica may have an average particle diameter ranging from about 3 to 70 microns and an average pore size of about 50 to 1000 Angstroms.

In a preferred aspect of the invention the matrix material contains from about 0.3 to 1.2 milliequivalents carboxy per gram matrix material.

In one embodiment, the contacting step of the invention is conducted at a pH of from about 4.0 to 6.0, but preferably at about 5.6. The releasing step may be carried out at a pH of greater than 6.0 and at an ionic strength of about 250 mM or above, preferably about 500 mM. The releasing step also may be conducted at a pH of less than about 4.0. Both the contacting and releasing steps may be conducted in the presence of epsilon amino caproic acid (EACA) and a detergent in a preferred aspect of the invention.

By practicing the method of the present invention, 90% or more of the urokinase in a urokinase compound-containing solution which has contacted the matrix material often can be recovered.

BRIEF DESCRIPTION OF THE DRAWING

The foregoing and other objects of this invention, the various features thereof, as well as the invention itself, may be more fully understood from the following description, when read together with the accompanying drawings.

DESCRIPTION OF THE INVENTION

Figure 1:
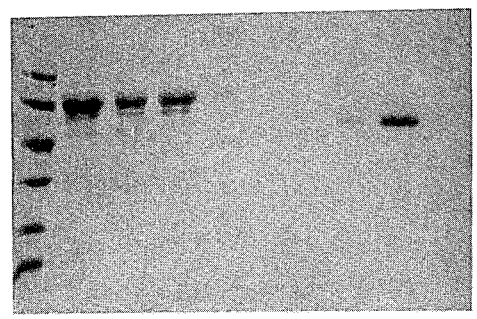
FIG. 1 is a representative Coomassie blue-stained SDS polyacrylamide gel of the fractions obtained by the chromatography of conditioned, serum-supplemented growth medium on an ABx column. Lane 1 contains low molecular weight standards; lane 2 contains the unfiltered starting material; lane 3 contains the filtered starting material loaded onto the column; lane 4 contains flow through; lane 5 contains Buffer A wash; lane 6 contains eluate obtained upon washing with 20% Buffer B in Buffer A; lane 7 contains Fraction 1 eluate material obtained upon development with 100% Buffer B; lane 8 contains Fraction 2 eluate material also obtained upon development with 100% Buffer B; lane 9 contains Fraction 3 eluate also obtained upon development with 100% Buffer B; and lane 10 contains eluate from the 100% Buffer C wash.

An efficient method of recovering undegraded urokinase compounds from urokinase compounds containing solutions has been devised which is simple, effective, and inexpensive.

The method utilizes affinity chromatographic and extraction procedures which take advantage of the unexpected finding that known resins of the type previously used to purify and separate immunoglobulins (see U.S. Pat No. 4,606,825) can be used to bind a urokinase compound preferentially and elute it differentially. In brief, the method comprises contacting a urokinase compound-containing solution with the resin under conditions conducive to protein binding, separating unbound protein from the resin, and releasing bound urokinase compound therefrom. The method can be used to recover urokinase from any solution which contains a urokinase compound by itself or in a mixture with other proteins. Such solutions include, for example, extracts of cells which express prourokinase, but which do not secrete it, and culture media which are serum-supplemented or serum-free. The SDS polyacrylamide gels shown in FIGS. 1 and 2 demonstrate the ability of the method to cleanly purify urokinase compounds from other protein constituents of the medium including serum albumin.

The type of separation material suitable for use in the purification process comprises a particulate, silicaceous matrix such as one composed of silica gel or glass beads. These component particles may be of any size known to be useful in performing recovery procedures. However, silica particles having a diameter ranging from about 3 to about 70 microns, and glass beads having a diameter ranging from about 35 to about 180 microns are preferred. An average particle diameter of about 40 microns is the most useful for performing the method of the present invention. The particles also may be porous, the silica gel having a preferred pore diameter ranging from about 50 to 1000 Angstroms, and the glass beads having a preferred pore diameter ranging from about 40 to 1000 Angstroms.

Bound to the silicaceous particles are one or more polymers which have multiple anionic groups. The preferred polymers are polyethylene derivatized with carboxylate. The polymer is preferably bound to the matrix through a silane group, and thus carboxylated polyethylenes having terminal reactive silane groups may be used to produce the separation matrix. The preferred polymer is a carboxylated polyethyleniminoalkyl silane such as a polyethyleniminopropyl trimethoxy silane. The molecular weight of the polymer generally may range from about 300 to about 2,000 daltons or higher. Although many different chemical side groups having a net negative charge may be useful, the most preferred anionic groups are carboxylate groups. A derivatized matrix material containing from about 0.3 to about 1.2 carboxy equivalents is the most desirable resin to effectively perform the method of the present invention.

The currently preferred matrix material useful in the present invention is sold by the J.T. Baker Chemical Co., Phillipsburg, N.J., under the trademark BAKERBOND ABx ™. This material comprises a silica gel having an average particle diameter of 40 microns derivatized with a carboxylated polyethylenimine polymer. The method of manufacture of this preferred material and additional details about its structure are disclosed in U.S. Pat. No. 4,540,486, the disclosure of which is incorporated herein by reference.

The contacting step of the method of the present invention may be performed in any way which allows the charged groups of the derivatized matrix to come into contact with the solution. One preferred way of performing the contacting step employs a chromatographic separation technique such as HPLC or traditional low pressure liquid chromatography wherein the urokinase-containing solution is passed over and through the matrix. This can be accomplished by preloading the matrix into a chromatographic column pre-equilibrated with a buffer conducive to binding (equilibration buffer), and pouring the urokinase-containing solution therethrough. The matrix material in the column may then be freed of extraneous material by washing with additional equilibration buffer.

An alternative contacting step uses a solid phase extraction procedure whereby the urokinase-containing solution is mixed together with the matrix, forming a two phase mixture. The liquid and solid phases are then separated, and the matrix material is resuspended in additional equilibration buffer to remove extraneously-bound proteins therefrom.

In either case, the contacting step must be performed under conditions which enable the binding of urokinase compounds in the solution to the derivatized matrix. Binding appears to be the result of the attraction and interaction of oppositely charged groups of the matrix and the urokinase compound. Therefore, conditions which maintain the charged nature of the urokinase compound and the matrix are important for success. Such conditions may be achieved by exposing the urokinase compound and the matrix to solutions of suitable pH and ionic strength. For example, growth media used to culture prourokinase-producing cells and containing urokinase compounds (conditioned medium) may be adjusted with acid such that the final pH is compatible with urokinase binding. In addition, the conditioned medium can be filtered to remove cell debris, and can be supplemented with a detergent, e.g., Tween-80, (Sigma Chemical Co.) to discourage aggregation of protein. Preferred conditions for binding include the use of a solution or equilibration buffer having a pH between about 4.0 and about 6.0, with a pH of about 5.6 being the most preferable.

The matrix containing bound protein is then washed, e.g., with an equilibration buffer, to remove extraneous proteins and other contaminants.

The urokinase releasing step must be carried out under specific conditions of ionic strength and pH to promote the most efficient removal of the bound urokinase compound from the matrix. This step may be conducted by exposing the urokinase compound bound to the matrix to a solution (i.e., an elution buffer) which causes its release. For example, the solution may be poured through a column containing the bound urokinase and matrix material or used to resuspend bulk matrix material. Exemplary solutions are an elution buffer having a pH greater than about 6.0 and an ionic strength greater than about 250 mM with an ionic strength of 500 mM being preferred. Alternatively, a urokinase compound may be eluted using a buffer having a pH of less than about 4.0. More than one elution buffer with increasing ionic strengths may also be used in sequence during the releasing step of the present invention.

Conditions which may enhance the success of the contacting and releasing steps may be instituted, including, for example, the addition of epsilon amino caproic acid (EACA), which acts as a protease inhibitor, and a detergent such as Tween-80 (Sigma Chemical Co.) to both the urokinase compound-containing solution and the eluant.

The amount of urokinase compounds recovered from a solution by the method of the present invention may be determined by any number of known assay methods including, for example, immunoassay or activity assays.

To measure activity, inactive prourokinase must first be converted to enzymatically active urokinase. This can be accomplished by a protease such as, for example, plasmin. The action of the protease must then be arrested by an inhibitor, for example, aprotinin. The protein remaining is urokinase, whose enzymatic activity can then be measured spetrophotometrically using a chromogenic substrate such as, for example, S-2444.

Generally, the method of the invention is able to recover in excess of 90% of the urokinase activity in the crude extract, and results in solutions having very high enzymatic activity.

The following examples are presented to illustrate, but not to limit, the subject matter of the invention.

EXAMPLE 1

In this example, prourokinase is extracted from a typical growth medium containing 1% fetal bovine serum (FBS), and 10 KI units/ml aprotinin.

A. Pre-treatment

Encapsulated, genetically engineered cells which produce human prourokinase are cultured in a growth medium, referred to hereinafter as "conditioned" (e.g., urokinase compound-containing) medium. The conditioned, isotonic medium is treated with EDTA to 5 mM and Tween 80 to 0.01%. The medium is then titrated to pH 5.6 with 6 N HCL, and filtered to remove cell debris.

B. Chromatography 7 liters of the pre-treated, conditioned medium are loaded at room temperature onto a Pharmacia K column (volume=41 ml) containing ABx (J.T. Baker Chemical Co., Phillipsburg, NJ; 40 micron particle diameter), and run at 105cm/hr. The column is washed with 10 column volumes of Equilibration Buffer A (10 mM morpholino ethane sulfonate (MES), 5 mM EDTA, and 0.01% Tween 80, pH 5.6.) and then 10 column volumes of 20% Elution Buffer B (500 mM NaOAc, 5 mM EDTA, 0.01% Tween 80, pH 7.0)/80% Buffer A. The protein on the column is eluted with 8 column volumes of 100% Buffer B. The column is then washed with 10 column volumes of Buffer C (1 M NaOAc, 5 mM EDTA, 0.01% Tween 80, pH 7.0). The column eluate is monitored by UV absorption at 280 nm.

C. Electrophoresis

The conditioned medium and column eluate are analyzed at different steps during the purification procedure by sodium dodecyl sulfate-polyacrylamide gel electrophoresis (SDS-PAGE) in accordance with the procedure of Laemmli (Nature (1970) 227:680-685). The 7.5%-20.0% gradient gel is stained with 0.25% Coomassie blue, 50% methanol, 10% acetic acid, destained with 50% methanol, 10% acetic acid, and photographed.

Most of the prourokinase eluting from the column is found in the column fractions containing peak 2 material in 100% Elution Buffer B, as shown in FIG. 1. FIG. 1 also demonstrates that the prourokinase has been cleanly separated and purified from other proteins in the culture medium.

D. Activity Assay

The medium and each of the column fractions analyzed by SDS-PAGE are analyzed for urokinase activity by the Direct Urokinase (UK) Assay as follows. Prourokinase has no enzymatic activity, and therefore must be converted to urokinase (active) by the action of plasmin.

$10\mu l$ of assay buffer (50 mM Tris-HCl, pH 7.5, 12 mM NaCl, 0.1% Triton X-100) are placed into the first well of a microtitre plate (Costar #2797 as a reagent blank. A urokinase standard stock solution (3000 IU/ml assay buffer Calbiochem #672081 is further diluted in assay buffer to 100, 50, 25, 12.5, and 6.25 IU/ml.

The diluted urokinase standards or unkown samples are added to the wells in triplicate. $2\mu l$ of plasmin (12.5 Casein units/ml $H_2O$ Helena #5303) is then added to appropriate wells. All samples are assayed in the presence and absence of plasmin. The samples are incubate for 1 hour at 37 degrees Celcius. To the positive plasmin plate is added 10 $\mu l$/well of aprotinin (2000 KIU/ml assay buffer, Sigma #A1153); to the negative plasmin plate is added 10 $\mu l$ assay buffer. Plates are incubated for 15 minutes at 37 degrees Celcius.

90 $\mu l$ of a 1 mM S-2444 (Helena #5281) in assay buffer solution is added to each well, and the plate incubated at 37 degrees for 2 to 3 hours. The optical density at 405 nm is read in a plate reader.

The concentration of prourokinase in the unknown samples is determined from a plot of enzyme units per well versus $OD_{405}$. The activity of the samples assayed in the presence of plasmin includes the sum of the activities of the prourokinase and urokinase present. The quantity of prourokinase in a given sample is the difference between the values obtained in the presence and absence of plasmin.

The results are shown below in Table 1.

TABLE 1

| | Urokinase Activity Assay | |
| --- | --- | --- |
| FRACTION | VOLUME | % OF TOTAL |
| orig pre-filter | 7000.0 ml | |
| orig material post filter | 7000.0 ml | 100% |
| Flow thru | 7000.0 ml | 0 |
| Wash | 1000.0 ml | 0 |
| 20% B:A | 1000.0 ml | 0 |
| 100% B | | |
| (Fraction 1) | 12.5 ml | 0 |
| (Fraction 2) | 30.0 ml | 0.7% |
| (Fraction 3) | 300.0 ml | 90.7% |
| 100% C | 1000.0 ml | 0 |

91.4% recovery of activity from the column

EXAMPLE 2

Pre-treatment

In this example prourokinase is extracted from a typical serum-free growth medium containing 10 Kl units/ml aprotinin, and is pre-treated and filtered as described in Example 1.

B. Chromatography 6 liters of the pre-treated, conditioned, isotonic medium are loaded at room temperature onto a Pharmacia K column (5×2.5 cm) containing ABx (J.T. Baker Chemical Co.; 40 micron particle diameter), and the column is run at 107 cm/hr. After loading, the column is washed with 20 column volumes of Buffer A, and 10 column volumes of 20% Buffer B/80% Buffer A. The protein on the column is eluted with 6 column volumes of 100% Buffer B (see Example 1). The column is then washed with 10 column volumes of 100% Buffer C.

The column eluate is monitored by UV absorption as described in Example 1. Two peak fractions are obtained upon development with 100% Buffer B.

C. Electrophoresis

Figure 2:
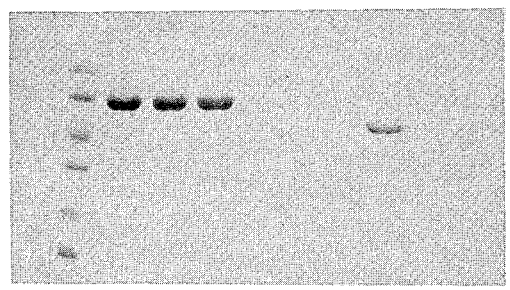
FIG. 2 is a representative Coomassie blue-stained SDS polyacrylamide gel of the fractions obtained by the chromatography of conditioned, serum-free growth medium on an ABx column. Lane 1 contains low molecular weight standards; lane 2 contains the unfiltered starting material; lane 3 contains the filtered starting material loaded on the column; lane 4 contains flow through; lane 5 contains Buffer A wash; lane 6 contains eluate obtained upon washing with 20% Buffer A in Buffer B; lane 7 contains Fraction 1 eluate material obtained upon development with 100% Buffer B; lane 8 contains Fraction 2 eluate material also obtained upon development with 100% Buffer B; and lane 9 contains eluate obtained upon development with 100% Buffer C.

The medium and column eluates are analyzed during the procedure by SDS-PAGE generally as described in Example I. The majority of the urokinase is eluted from the column with 100% Buffer B as shown in FIG. 2.

D. Activity Assay

The enzymatic activity of the urokinase found in the medium and column eluate at each step during the procedure is analyzed by the Direct UK Assay as described above in Example 1.

TABLE 2

| FRACTION | Urokinase Activity Assay | |
|---|---|---|
| | VOLUME | % OF TOTAL |
| orig pre-filter | 6000.0 ml | |
| orig material post filter | 6000.0 ml | 100% |
| Flow thru | 6000.0 ml | 0 |
| Wash 100% A | 1000.0 ml | 0 |
| Wash 20% B:A | 490.0 ml | 0 |
| 100% B (Fraction 1) | 65.0 ml | 0.1% |
| 100% B (Fraction 2) | 215.0 ml | 91.0% |
| 100% C | 500.0 ml | 0 |

91.1% recovery of activity from the column

EXAMPLE 3 A. Pre-treatment:

In this example, prourokinase is extracted from a typical serum-free growth medium containing 10 KI units/ml aprotinin, and is pre-treated and filtered as described in Example 1.

B. Chromatography 8 liters of the pre-treated, conditioned, medium are loaded at room temperature onto a Pharmacia K column (5×2.0 cm) containing ABx (J.T. Baker Chemical Co.; 40 micron particle diameter), and the column is run at 105 cm/hr. After loading, the column is washed with 10 column volumes of Buffer A, and 10 column volumes of 20% Buffer B/80% Buffer A. The protein on the column is eluted with 8 column volumes of 100% Buffer B (see Example 1). The column is then washed with 10 column volumes of 100% Buffer C.

The column eluate is monitored by UV absorption as described in Example 1. Two peak fractions are obtained upon development with 100% Buffer B.

C. Electrophoresis

The medium and column eluates are analyzed during the procedure by SDS-PAGE generally as described in Example I. The majority of the prourokinase is eluted from the column with 100% Buffer B (Fraction 2).

D. Activity Assay

The enzymatic activity of the urokinase found in the medium and column eluate at each step during the procedure is analyzed by the Direct UK Assay as described above in Example 1.

The results are shown below in Table 3.

TABLE 3

| FRACTION | Urokinase Activity Assay | |
|---|---|---|
| | VOLUME | % OF TOTAL |
| orig pre-filter | 8000.0 ml | |
| orig material post filter | 8000.0 ml | 100% |
| Flow thru | 8000.0 ml | 0 |
| Wash 100% A | 400.0 ml | 0 |
| Wash 20% B:A | 400.0 ml | 0 |
| 100% B (Fraction 1) | 20.0 ml | 0 |
| 100% B (Fraction 2) | 300.0 ml | 99.5% |
| 100% C | 400.0 ml | 0 |

99.5% recovery of activity from the column

As can be appreciated from the foregoing examples, most if not all of the urokinase-related enzymatic activity can be recovered from both serum-free and serum-supplemented medium by the method of the present invention.

What is claimed is:

1. A method for extracting a urokinase compound from a solution of urokinase compounds and other proteins, said method comprising the steps of:
   (a) contacting a urokinase compound-containing protein solution with a particulate, silicaceous matrix under conditions in which a urokinase compound in said solution binds to said matrix, said matrix comprising the covalently bound, carboxylated reaction product of said particulate, silicaceous matrix with polyethyleniminopropyl trimethoxy silane;
   (b) separating unbound protein from said matrix; and
   (c) releasing a urokinase compound from said matrix.

2. The method of claim 1 wherein said solution comprises a culture medium.

3. The method of claim 1 wherein said solution comprises a cell extract.

4. The method of claim 1 wherein said contacting step is conducted by passing said urokinase compound-containing solution over said matrix using a chromatographic separation technique.

5. The method of claim 1 wherein said contacting step is conducted by mixing together said matrix and said urokinase compound-containing solution to form a two-phase mixture using a solid phase extraction technique.

6. The method of claim 1 wherein said silicaceous matrix comprises particles selected from the group consisting of silica gel and porous glass beads.

7. The method of claim 6 wherein said matrix material comprises from about 0.3 to about 1.2 carboxyl milliequivalents per gram of said matrix material.

8. The method of claim 1 wherein said contacting step is conducted at a pH between about 4.0 and about 6.0.

9. The method of claim 12 wherein said contacting step is conducted at a pH of about 5.6.

10. The method of claim 1 wherein said releasing step is conducted at a pH greater than about 6.0 and at an ionic strength greater than about 250 millimolar.

11. The method of claim 14 wherein said releasing stop is conducted at an ionic strength of about 500 millimolar.

12. The method of claim 1 wherein said releasing step is conducted at a pH less than about 4.0.

13. The method of claim 1 wherein said contacting and releasing steps are conducted in the presence of epsilon amino caproic acid and a detergent.

14. The method of claim 1 wherein said releasing step produces a fraction wherein a urokinase compound therein constitutes at least 90% of the urokinase compounds in said urokinase compound-containing solution which has contacted said matrix.

* * * * *